Figure 1:
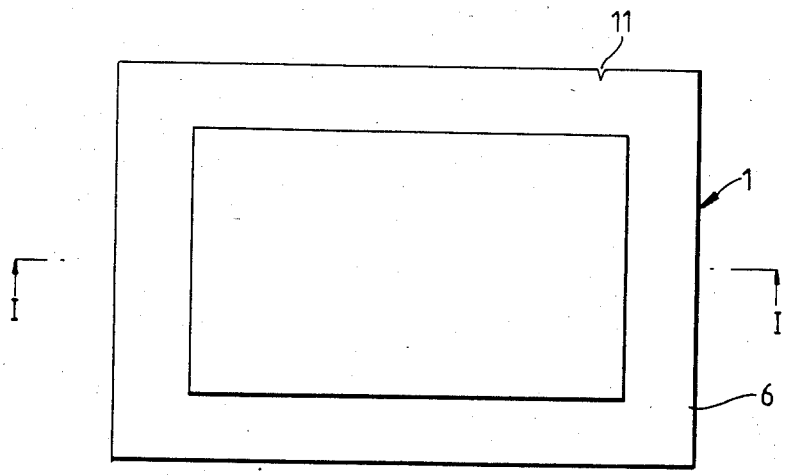

United States Patent [19]

Gray

[11] Patent Number: 4,594,835
[45] Date of Patent: Jun. 17, 1986

[54] METHOD FOR MAKING SACHETS

[75] Inventor: Roy F. Gray, Macclesfield, United Kingdom

[73] Assignee: Imperial Chemical Industries PLC, London, England

[21] Appl. No.: 536,450

[22] Filed: Sep. 28, 1983

Related U.S. Application Data

[62] Division of Ser. No. 287,809, Jul. 28, 1981.

[30] Foreign Application Priority Data

Aug. 11, 1980 [GB] United Kingdom ................. 8026059

[51] Int. Cl.⁴ .............................................. B65B 31/02
[52] U.S. Cl. ........................................ 53/433; 53/436; 53/453; 53/474
[58] Field of Search ................. 53/239, 432, 433, 434, 53/436, 453, 471, 474, 527

[56] References Cited

U.S. PATENT DOCUMENTS

| | | |
|---|---|---|
| 2,232,783 | 2/1941 | Hausheer . |
| 2,613,862 | 10/1952 | Vaughn . |
| 3,035,300 | 5/1962 | Wattles ................................ 15/563 |
| 3,082,468 | 3/1963 | Wattles . |
| 3,174,654 | 3/1965 | Reiner . |
| 3,429,096 | 2/1969 | Griese ................................ 53/471 |
| 3,537,226 | 11/1970 | Le Van et al. .................... 53/434 X |
| 3,618,283 | 11/1971 | Moore et al. ..................... 53/474 X |
| 4,157,787 | 6/1979 | Schwartz ......................... 239/60 X |
| 4,229,927 | 10/1980 | Day .................................... 53/433 |
| 4,372,098 | 2/1983 | Mason .............................. 53/478 X |
| 4,424,659 | 1/1984 | Perigo et al. ..................... 53/527 X |

FOREIGN PATENT DOCUMENTS 2436504 7/1974 Fed. Rep. of Germany .

*Primary Examiner*—Robert L. Spruill
*Assistant Examiner*—Michael D. Folkerts
*Attorney, Agent, or Firm*—Cushman, Darby & Cushman

[57] ABSTRACT

A sachet which comprises a sealed bag containing a compressible and porous carrier which is held under compression within the sachet by pressure exerted by the walls of the sachet onto the carrier, the carrier being thoroughly impregnated with liquid suitably an antiseptic. Methods are provided for manufacture of the sachets. The carriers in such sachets containing antiseptic liquid have reduced tendency to harbor bacteria, and are preferably open or reticulated cell foam sponges.

4 Claims, 2 Drawing Figures

METHOD FOR MAKING SACHETS

This is a division, of application Ser. No. 287,809, filed July 28, 1981.

This invention relates to sachets and in particular to sachets which contain an impregnated substrate.

Sachets which are small sealed bags made from impermeable plastic film or metal foil have been known for many years. Such sachets have a variety of uses such as for example in the food industry for dispensing of individual portions of liquids and pastes, e.g. mayonaise, ketchup, and of solid materials such as cheese and butter; also in the cosmetic and toiletry industries for containing small volumes of shampoo, skin conditioners and refresher wipes which comprise generally nonwoven fabric impregnated with small quantities of liquid containing a mild detergent and a perfume.

There has however been a need in the medical, and in particular surgical art for a sachet containing a wipe which will not harbour bacteria and which contains a larger quantity of liquid than hitherto such as an antiseptic liquid for hand washing of staff prior to surgery.

According to the present invention a sachet is provided which comprises a sealed bag containing a compressible and porous carrier which is held under compression within the sachet by pressure exerted by the walls of the sachet onto the carrier, the carrier being thoroughly impregnated with liquid, suitably an antiseptic liquid.

The carrier is made from compressible porous material such as for example, felt, cotton wool, layers of bandage, melded fabric, pile or fleece surfaced material, entangled, knitted or needle-punch material but is preferably a sponge having an open or reticulated cell structure. Such structures are well known in the art. Hitherto an open cell foam has generally not been found suitable for such an antiseptic sponge because it generally has too slow an uptake of liquid for satisfactory impregnation during manufacture and distribution of the liquid throughout the foam is not thorough; indeed parts may be dry and hence harbour bacteria. However reticulated foam may be used but is less desirable on cost grounds. Suitable foam may be made from polyester and preferably polyether polyurethane. One face of the carrier may be provided with other cleaning aids such as a moulded brush or scouring or scrub foam pad if desired.

Sachets are generally made from plastic film or metal foil preferably having thickness between 50 μm and 300 μm which are capable of being sealed by heat sealing or less desirably an adhesive, radio-frequency or ultrasonic means to form the sachet bag. Very often laminates are used to combine desirable properties of the films and foils. For example polyethylene terephthalate/low density polyethylene laminate, nylon/low density polyethylene are conventional laminates; the polyethylene is used principally to effect a good heat seal between two adjacent pieces of laminate which form the walls of the sachet. A metal foil laminate may be used in place of a film to provide, e.g. low permeability, good decorative effect but such foil laminates are less easy to pre-form.

The sachet of the present invention may be made by forming a dish-like pocket in a sheet of film or foil, placing a measured amount of liquid, suitably an antiseptic into the pocket, placing a piece of carrier having base area smaller than the base area of the pocket into the pocket, placing a second film or foil over the pocket which contains the liquid and piece of carrier to form an assembly, evacuating the pocket and around the assembly below atmospheric pressure, heat sealing the second film or foil around the edge of the pocket to form a sachet and releasing the vacuum around the sachet. Atmospheric pressure will cause the pocket to decrease in volume, and compress the carrier. The carrier takes up further quantities of antiseptic liquid in the sachet and expands on withdrawal from the open sachet. Penetration of liquid into the carrier may be assisted by manipulation, for example compression through nip rolls, of the sachet or pressure cycling. Suitably the vacuum will be in the range 50 to 650 mm of mercury, preferably 150 to 450 mm of mercury, although the vacuum may eventually be chosen according to the desired degree of compression.

In an alternative embodiment the piece of carrier may have height greater than the depth of the pocket whilst its base area is less than that of the pocket. In manufacturing such a sachet the carrier is compressed by pressure applied preferably to the second or upper film or foil before evacuation and sealing steps. Such a sachet generally has an improved appearance.

It is envisaged for such commercial production of the present sachet, a continuous process would be carried out in which pockets are produced as parts of a continuous web of film or foil, and measured amounts of antiseptic solution and carriers are placed into the pockets at stations along the web as the web passes the stations. Thereafter a second web, possibly printed would be placed over the web containing the pockets, followed by the evacuation stage, the sachet formed by heat sealing the two webs around each pocket, releasing the vacuum and separating the sachets as required by cross and/or longitudinal cutting between adjacent sachets.

The present invention has an advantage therefore over an alternative sachet produced by impregnating a reticulated foam sponge by squeezing and dipping the squeezed sponge into antiseptic solution and releasing the sponge followed by wrapping or forming a sachet around that impregnated sponge in that voids containing no antiseptic are formed in such a sponge so leading to a possibility of spread of infection in use.

A suitable antiseptic solution contains chlorhexidine gluconate in water at a concentration of about 4% by weight. Such a solution is available as 'Hibiscrub' (Imperial Chemical Industries PLC).

Figure 2:
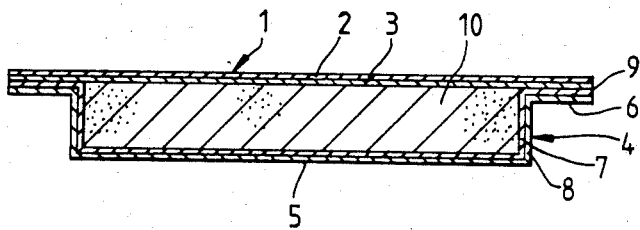

The invention is illustrated with reference to the accompanying figures in which FIG. 1 is a top plan of a sachet according to the invention and FIG. 2 is a section on the line I—I of FIG. 1.

The sachet was produced as follows. A pocket having depth 25 mm., length 90 mm., and width 60 mm., was formed with a surrounding shoulder by evacuating a sheet of laminate into similar sized mould. Antiseptic solution (20 cm.$^3$; 'Hibiscrub' (Imperial Chemical Industries PLC) was placed into the pocket. A piece of reticulated cell polyether polyurethane foam (30 pores per linear cm., density 0.0015 g/cm.$^3$) having length and width slightly smaller than those of the pocket but similar height to pocket depth was placed into the pocket containing antiseptic solution. A top film or foil was placed above the pocket so as to overlap onto the surrounding shoulder to form an assembly. The chamber containing the assembly was evacuated to a pressure of 350 mm mercury substantially retaining the original dimensions; then the top film or foil was heat-sealed to the surrounding shoulder. After heat-sealing, the vacuum was released and the sachet pocket reduced in volume by half its original volume so compressing the foam sponge. On opening the sachet, the foam resumed its original size and contained almost all the liquid; examination of the foam showed that it had been thoroughly wetted with the liquid.

With reference to FIGS. 1 and 2, the sachet comprises a top foil (1) which is a laminate of two films (2, 3) of which (2) is made from biaxially oriented polyethylene terephthalate (thickness 12 μm; draw ratio 3.3:1 in both directions) and film (3) is made from low density polyethylene (thickness 50 μm). The bottom foil (4) is provided with a pocket (5) and surrounding shoulder (6) and also a laminate of two films (7, 8) of which film (7) is made from low density polyethylene (thickness 70 μm) and film (8) is made from nylon (thickness 30 μm). The top and bottom foils are sealed together through heat seals (9) on the shoulder. Impregnated sponge (10) is located within the pocket and held under compression mainly by the top foil (1) and the base of pocket (5). A V-notch (11) is provided to facilitate opening of the sachet and removal of the impregnated sponge (10). It will be appreciated that the present sachet will have some ridges or loose folds in the walls, base and top as they concertina from the effect of atmospheric pressure after releasing the vacuum.

I claim:

1. A method for making a sachet which comprises forming a dish-like pocket in a sheet of film or foil, placing a measured amount of liquid into the pocket, placing a carrier comprised of compressible porous material into the pocket, absorbing a first part of said measured amount of liquid into said carrier which is placed into said pocket, placing a second film or foil over the pocket which pocket contains the liquid and piece of carrier to form an assembly, evacuating the pocket and around the assembly below atmospheric pressure, sealing the second film or foil around the edge of the pocket to form a sachet, and decreasing the volume of the carrier, compressing the carrier and forcing an additional quantity of liquid into the carrier by releasing the vacuum around the sachet.

2. A method as claimed in claim 1 which is an essentially continuous process comprising forming pockets from a continuous web of film or foil, placing measured amounts of liquid and carriers into the pockets at stations along the web as the web passes those stations, placing a second web of film or foil over the web containing the pockets to form a local assembly, evacuating the assembly, forming a sachet by sealing the two webs around the pocket, releasing the vacuum and separating the sachets.

3. A process as claimed in claim 1 in which the carrier has height greater than the depth of the pocket and is partially compressed before forming the sachet by pressure applied onto the carrier.

4. A method as claimed in claim 1 in which the sealing is achieved by heat.

* * * * *